(12) United States Patent
Ellis et al.

(10) Patent No.: US 7,915,184 B2
(45) Date of Patent: Mar. 29, 2011

(54) ANTI-MICROBIAL NONWOVEN WIPE

(75) Inventors: Dianne Ellis, Cary, NC (US); Jimmy D. West, Coats, NC (US); Jennifer Mayhorn, Huntersville, NC (US); Nick Carter, Mooresville, NC (US)

(73) Assignee: Polymer Group, Inc., Charlotte, NC (US)

( * ) Notice: Subject to any disclaimer, the term of this patent is extended or adjusted under 35 U.S.C. 154(b) by 735 days.

(21) Appl. No.: 10/699,425

(22) Filed: Oct. 31, 2003

(65) Prior Publication Data

US 2004/0137815 A1   Jul. 15, 2004

Related U.S. Application Data

(60) Provisional application No. 60/422,786, filed on Oct. 31, 2002.

(51) Int. Cl.
*B32B 27/12* (2006.01)

(52) U.S. Cl. .................. 442/123; 442/124; 442/35

(58) Field of Classification Search .............. None
See application file for complete search history.

(56) References Cited

U.S. PATENT DOCUMENTS

| | | | |
|---|---|---|---|
| 4,929,498 A | 5/1990 | Suskind et al. | |
| 4,931,355 A | 6/1990 | Radwanski et al. | |
| 5,421,898 A | 6/1995 | Cavanagh | |
| 5,475,903 A | 12/1995 | Collins | |
| 5,522,942 A * | 6/1996 | Graubart et al. | 134/40 |
| 6,015,836 A | 1/2000 | Martin | |
| 6,667,290 B2 * | 12/2003 | Svendsen | 510/438 |
| 6,734,157 B2 * | 5/2004 | Radwanski et al. | 510/439 |
| 6,735,833 B2 * | 5/2004 | Putnam et al. | 28/104 |
| 6,878,648 B2 * | 4/2005 | Mayhorn et al. | 442/64 |
| 6,916,480 B2 | 7/2005 | Anderson et al. | |
| 6,916,776 B2 | 7/2005 | Svendsen | |
| 7,013,541 B2 * | 3/2006 | Rivera et al. | 28/104 |
| 2002/0022050 A1 | 2/2002 | Anderson et al. | |
| 2004/0228904 A1 * | 11/2004 | Ellis et al. | 424/443 |

FOREIGN PATENT DOCUMENTS

| | | |
|---|---|---|
| GB | 2330765 A | 5/1999 |
| WO | 0148303 A2 | 7/2001 |
| WO | 02077345 A2 | 10/2002 |

OTHER PUBLICATIONS

Supplementary European Search Report, European appln. No. EP 03 781 629, Jul. 31, 2007, 2 pages.
European examination communication, European appln. No. EP 03 781 629, Nov. 19, 2007, 6 pages.

* cited by examiner

*Primary Examiner* — Arti Singh-Pandey
(74) *Attorney, Agent, or Firm* — Kilyk & Bowersox, P.L.L.C.; Valerie Calloway

(57) ABSTRACT

The present invention is directed to a nonwoven anti-microbial hard surface wipe, and more specifically to an anti-microbial hard surface wipe that more readily releases a disinfectant or anti-microbial agent. In a first embodiment, the nonwoven substrate of the present invention is comprised of a non-ionic binder, as well as a cationic disinfectant. The wipe is introduced into a water source and the disinfectant is readily released from the wipe so as to form a disinfectant solution. In a second embodiment, the nonwoven substrate of the present invention is comprised of a non-ionic binder and used along with a separate commercially available disinfecting or sanitizing solution. The disinfecting solution is preferably a cationic disinfecting solution, such as a cationic dual quaternary sanitizing system.

9 Claims, 1 Drawing Sheet

ANTI-MICROBIAL NONWOVEN WIPE

TECHNICAL FIELD

Figure 1:
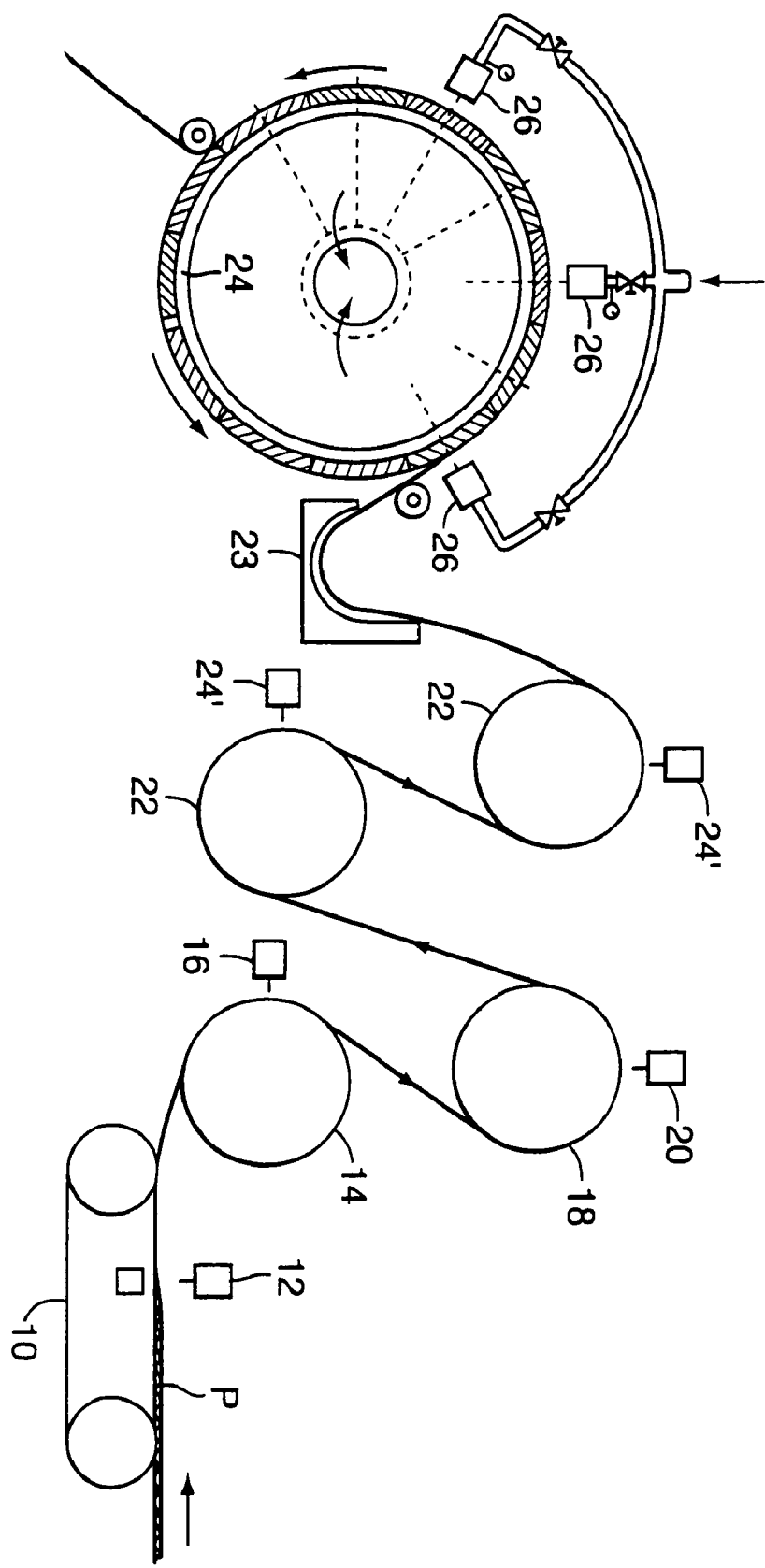

The present invention generally relates to a nonwoven anti-microbial hard surface wipe, and more specifically to an anti-microbial hard surface wipe that more readily releases a disinfectant or anti-microbial agent.

BACKGROUND OF THE INVENTION

Over the years, the use of disposable substrates in cleaning applications has been well practiced. Suitable substrates have included sponges, woven and nonwoven fabrics, and various combinations thereof. Further, such substrates have been impregnated with cleaning agents such as disinfectants, solvents, anti-microbials, detergents and other chaotropes. The resulting cleaning products fabricated from such impregnated substrates have found acceptance with the general public as a convenient and practical means for the cleaning of surfaces. In particular, such constructs have been successful in the consumer wipes markets as hard surface wipes.

Nonwoven fabrics are used in a wide variety of wipe applications where the engineered qualities of the fabrics can be advantageously employed. The use of selected thermoplastic polymers in the construction of the fibrous fabric component, selected treatment of the fibrous component (either while in fibrous form or in an integrated structure), and selected use of various mechanisms by which the fibrous component is integrated into a useful fabric, are typical variables by which to adjust and alter the performance of the resultant nonwoven fabric.

For the purpose of fabricating a hard surface wipe for the food service or hospitality industry, it is advantageous to utilize a limited or single use nonwoven wipe to prevent the build up of bacteria that tends to accumulate within a standing damp sponge or terry cloth towel. Upon repeated use of a standing damp sponge, it is more likely that bacteria will be introduced into an area where food is prepared. Often, for the sake of convenience, the nonwoven wipe is impregnated or coated with an anti-microbial agent or disinfectant so as to prevent the growth of bacteria and disinfect food preparation areas. It has been found, however that nonwoven hard surface wipes that are impregnated or coated with an anti-microbial do not readily release the anti-microbial agent due to the affinity of the disinfectant for the nonwoven substrate itself, the binders utilized within the substrate, or the affinity for any other additives that may be present in the substrate.

The use of homogenous cationic binder in sanitation wipes has a deleterious affect on the sanitation process. Cationic binders are attracted or have a high affinity for an anionic charged disinfectant and results in a hard surface wipe that retains the disinfectant. The disinfectant solution is more rapidly absorbed into the wipe, which prematurely depletes the disinfectant solution of the anti-microbial attributes. Further, a wipe comprising a cationic binder may not properly absorb a cationic disinfectant due to the lack of affinity of the binder for the disinfectant. A nonwoven wipe that fails to absorb the disinfectant solution may not effectively sanitize a given surface.

Non-ionic binders do not have an associated positive or negative charge and are therefore compatible with various disinfecting or anti-microbial sanitizing systems. A hard surface wipe comprised of a non-ionic binder has a low affinity for an ionic disinfecting solution, which is beneficial to the sanitizing process. The wipe forms weak bonds with the disinfectant, thereby increasing the life of the sanitizing solution. There remains an unmet need for a hard surface wipe that is compatible with various ionic disinfecting solutions.

SUMMARY OF THE INVENTION

The present invention is directed to a nonwoven anti-microbial hard surface wipe, and more specifically to an anti-microbial hard surface wipe that more readily releases a disinfectant or anti-microbial agent.

The anti-microbial wipe of the invention is a nonwoven substrate. Suitable substrates include, but are not limited to hydroentangled, airlaid, spunbond, and coform substrates. Further, the nonwoven substrate could be a laminate or composite structure. The nonwoven wipe may be hydroentangled on a three-dimensional image transfer device in order to impart an aesthetically appealing pattern or image into the wipe, wherein the pattern or image may or may not include apertures. Further, the wipe may include a three-dimensional image of a restaurant or hospitality industry company logo.

In a first embodiment, the nonwoven substrate of the present invention is comprised of a non-ionic binder, as well as a cationic disinfectant. The wipe is introduced into a water source and the disinfectant is readily released from the wipe so as to form a disinfectant solution.

In a second embodiment, the nonwoven substrate of the present invention is comprised of a non-ionic binder and used along with a separate commercially available disinfecting or sanitizing solution. The disinfecting solution is preferably a cationic disinfecting solution, such as a cationic dual quaternary sanitizing system.

The hard surface wipe comprised of a non-ionic binder has a low affinity for a cationic disinfecting solution and the weak bonds formed are easily broken. The resulting wipe more readily releases the disinfectant into a water source and will not attract and retain a charged disinfectant that could possibly prematurely deplete the effectiveness of a sanitizing solution.

DETAILED DESCRIPTION

While the present invention is susceptible of embodiment in various forms, there is shown in the drawing, and will hereinafter be described, a presently preferred embodiment, with the understanding that the present disclosure is to be considered as an exemplification of the invention, and is not intended to limit the invention to the specific embodiment illustrated.

The present invention is directed to a method of forming an anti-microbial nonwoven wipe with a more readily releasable disinfecting or anti-microbial agent. The nonwoven wipe is comprised of a matrix of fibers or filaments that is consolidated into a nonwoven web. In a preferred embodiment, the nonwoven wipe is a hydroentangled substrate. With reference to FIG. 1, therein is illustrated an apparatus for practicing the present invention by forming a hydroentangled nonwoven fabric. The fabric is formed from a fibrous matrix, which typically comprises staple length fibers, but may comprise substantially continuous filaments. The fibrous matrix is preferably carded and cross-lapped to form a fibrous batt. In a current embodiment, the fibrous batt comprises 100% cross-lap fibers, that is, all of the fibers of the web have been formed by cross-lapping a carded web so that the fibers are oriented at an angle relative to the machine direction of the resultant web. U.S. Pat. No. 5,475,903, hereby incorporated by reference, illustrates a web drafting apparatus.

Alternately, the fabric of the present invention may comprise an optional support layer or scrim, wherein the fibrous web can be placed face-to-face with the support layer and hydroentangled to form precursor web P. It is within the purview of the present invention that a scrim can be interposed in the formation of the precursor nonwoven web. The purpose of the scrim is to reduce the extensibility of the resultant three-dimensional imaged nonwoven fabric, thus reducing the possibility of three-dimensional image distortion and further enhancing fabric durability. Suitable scrims include unidirectional monofilament, bi-directional monofilament, expanded films, and thermoplastic spunbond.

Further, the composite construct may optionally be subsequently subjected to a three-dimensional image transfer device so as to impart a three-dimensional image, which may or may not include apertures.

FIG. 1 illustrates a hydroentangling apparatus for forming nonwoven fabrics in accordance with the present invention. The apparatus includes a foraminous-forming surface in the form of belt 10 upon which the fibrous web P is positioned for entangling by entangling manifold 12. Further entanglement of the web is effected on the foraminous forming surface of a drum 18 by entanglement manifold 20, with the web subsequently passed over successive foraminous drums 20, for successive entangling treatment by entangling manifolds 24, 24'.

The entangling apparatus of FIG. 1 further includes a three-dimensional imaging drum 24, which can be optionally utilized, comprising a three-dimensional image transfer device for effecting imaging of the now-entangled precursor web. The image transfer device includes a moveable imaging surface which moves relative to a plurality of entangling manifolds 26 which act in cooperation with three-dimensional elements defined by the imaging surface of the image transfer device to effect imaging and patterning of the fabric being formed.

Manufacture of a nonwoven wipe embodying the principles of the present invention is initiated by providing the fibrous matrix, which can include the use of staple length fibers, continuous filaments, and the blends of fibers and/or filaments having the same or different composition. Fibers and/or filaments are selected from natural or synthetic composition, of homogeneous or mixed fiber length. Suitable natural fibers include, but are not limited to, cotton, wood pulp and viscose rayon. Synthetic fibers, which may be blended in whole or part, include thermoplastic and thermoset polymers. Thermoplastic polymers suitable for blending with dispersant thermoplastic resins include polyolefins, polyamides and polyesters. The thermoplastic polymers may be further selected from homopolymers; copolymers, conjugates and other derivatives including those thermoplastic polymers having incorporated melt additives or surface-active agents. Staple lengths are selected in the range of 0.25 inch to 10 inches, the range of 1 to 3 inches being preferred and the fiber denier selected in the range of 1 to 22, the range of 1.2 to 6 denier being preferred for general applications. The profile of the fiber and/or filament is not a limitation to the applicability of the present invention.

It is also within the purview of the present invention that the hard surface wipe comprise additional fabric layers so as to form a laminate construct. The additional layers may include, but are not limited to fabrics comprised of natural, synthetic fibers, or a combination thereof. Suitable natural fibers include, but are not limited to, cotton, wood pulp and viscose rayon. Synthetic fibers, which may be blended in whole or part, include thermoplastic and thermoset polymers. The thermoplastic polymers may be further selected from homopolymers; copolymers, conjugates and other derivatives including those thermoplastic polymers having incorporated melt additives or surface-active agents. Additionally, film layers may be added to form a laminate construct. Various film layers may include, cast films, extruded films, and reticulated films.

In one embodiment, subsequent to the nonwoven web formation, the web is treated with a binder, as well as an anti-microbial or disinfecting agent. The binder of the invention is a non-ionic binder or a mixture of a non-ionic and a cationic binder. The binder, as well as the anti-microbial cleaning agent may be applied utilizing various techniques known in the art, including, but not limited to impregnating, padding, spray coating, or kiss coating.

In another embodiment, the hard surface wipe is comprised of a non-ionic binder to be utilized with a separate commercially available disinfecting or anti-microbial solution. The wipe of the invention is more compatible with such solutions and will not retain the anti-microbial solution within the wipe, which could result in prematurely depleting the effectiveness of the disinfection solution.

Optionally, the anti-microbial nonwoven wipe may further include an additive or combination of additives, such as pigments, color stabilizers, softeners, fragrances, lotions, and other performance or aesthetic enhancers.

From the foregoing, numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

What is claimed is:

1. A nonwoven anti-microbial wipe comprising a fibrous nonwoven substrate coated with a non-ionic and cationic binder mixture and subsequently coated with a cationic dual quaternary ammonia anti-microbial agent, said cationic dual quaternary ammonia anti-microbial agent being readily released upon being introduced to an associated water source.

2. A nonwoven anti-microbial wipe as in claim 1, wherein said anti-microbial wipe is a hard surface wipe.

3. A nonwoven anti-microbial wipe as in claim 1, wherein said fibrous nonwoven substrate comprises natural fibers.

4. A nonwoven anti-microbial wipe as in claim 1, wherein said fibrous nonwoven substrate comprises natural fibers selected from the group consisting of cotton, wood pulp and viscose rayon.

5. A nonwoven anti-microbial wipe as in claim 1, wherein said fibrous nonwoven substrate comprises carded and cross-lapped staple length fibers.

6. A nonwoven anti-microbial wipe comprising:
   a three-dimensionally imaged fibrous nonwoven substrate coated with a non-ionic and cationic binder mixture and subsequently coated with a cationic dual quaternary ammonia anti-microbial agent, said cationic dual quaternary ammonia anti-microbial agent being readily released upon being introduced to an associated water source, and
   a scrim layer reducing the extensibility of said three-dimensionally imaged fibrous nonwoven substrate.

7. A nonwoven anti-microbial wipe as in claim 6, wherein said scrim layer is selected from a unidirectional filament scrim, a bi-directional filament scrim, an expanded film, and a thermoplastic spunbond.

8. A nonwoven laminate anti-microbial wipe comprising:
   a fibrous nonwoven substrate coated with a non-ionic and cationic binder mixture and subsequently coated with a cationic dual quaternary ammonia anti-microbial agent, said cationic dual quaternary ammonia anti-microbial agent being readily released upon being introduced to an associated water source, and an additional layer selected from the group consisting of a fabric layer and a film layer.

9. A nonwoven laminate anti-microbial wipe as in claim 8, wherein said additional layer is a film layer selected from the group consisting of a cast film, an extruded film, and a reticulated film.

* * * * *